United States Patent [19]

Jasso

[11] 4,413,636
[45] Nov. 8, 1983

[54] CATHETER

[75] Inventor: Martin R. Jasso, Houston, Tex.

[73] Assignee: Phillip R. Beutel, Colorado Springs, Colo.

[21] Appl. No.: 361,802

[22] Filed: Mar. 25, 1982

Related U.S. Application Data

[63] Continuation of Ser. No. 95,342, Nov. 19, 1979, abandoned.

[51] Int. Cl.³ .............................................. D61N 1/04
[52] U.S. Cl. .................................................. 128/786
[58] Field of Search .................... 128/419 PS, 784–786

[56] References Cited

U.S. PATENT DOCUMENTS

| | | | |
|---|---|---|---|
| 3,533,403 | 10/1970 | Woodson | 128/419 P |
| 3,735,766 | 5/1973 | Bowers et al. | 128/419 P |
| 3,749,101 | 7/1973 | Williamson | 128/786 |
| 4,161,952 | 7/1979 | Kinney et al. | 128/786 |
| 4,214,804 | 7/1980 | Little | 128/419 P |

Primary Examiner—William E. Kamm
Attorney, Agent, or Firm—Ned L. Conley; David Alan Rose; William E. Shull

[57] ABSTRACT

An electrode assembly for a catheter having first and second conductors comprises an anode ring including an outer portion and an inner portion connected to the outer portion. The inner portion includes a solid member having a blind passage therein and a channel therethrough. One end of the first conductor is received in the blind passage and retained therein by a pair of crimps impressed into the solid member against the conductor end. The second conductor extends through the anode ring in the channel. Alternatively, the inner portion includes a post which is received in a passage in the end of the first conductor and is welded to the first conductor. The second conductor includes a lead portion and a tip portion spaced therefrom and the anode ring includes a feed-through tube extending therethrough and interconnecting the lead and tip portions of the second conductor.

The outer anode ring portion includes a tubular part having a wall with an outer surface and an inner surface, and including an aperture extending through the wall from its outer surface to its inner surface. Some portions of such inner surfaces, or such inner and outer surfaces, are roughened.

The outer anode ring portion at one end includes a ring tip having a passage therethrough, such passage through such ring tip being coaxial with the anode ring and carrying such second conductor therewithin.

8 Claims, 21 Drawing Figures

CATHETER

This is a continuation of application Ser. No. 95,342, filed Nov. 19, 1979, now abandoned.

BACKGROUND OF THE INVENTION

1. Field of the Invention

The present invention relates generally to catheters having a bipolar electrode tip for transmitting electrical signals to and from a particular internal region of an animal's body and more specifically to catheters having a plug portion for connection to an electronics unit, an electrode portion for electrically contacting a portion of the animal's body, and a lead portion extending between the plug portion and the electrode portion, the lead portion including a pair of spiral conductors disposed in a bilumen tube, and the electrode portion including an anode ring and a cathode tip spaced from the anode ring, the cathode tip being electrically connected to one of the lead portion conductors and the anode ring being connected to the other of the lead portion conductors.

2. Background of the Prior Art

Transmission of electrical signals to and from various internal regions of an animal's body is an essential aspect of many modern diagnostic and corrective medical procedures and techniques. For example, the use of an artificial pacemaker in treating heart block, which is a failure of the body to provide the necessary electrical stimulus to maintain the steady rhythmic beating of the heart, includes transmitting electrical signals between a battery-powered electronic unit and the surface of the heart. In accordance with modern systems, the electronic unit senses an interruption in the heartbeat rhythm and, in response, transmits an electrical signal to the heart to stimulate the heart to its proper rhythm.

In the prior art, such procedures have been implemented using a system including an electronic unit and a catheter. The electronic unit generally has included an electronic circuit for sensing the existence or non-existence of body-produced electrical stimuli and/or for providing artificial electrical signal stimuli; a battery for powering the electronic circuit; and connector jacks for connecting the electronic circuit to the catheter. Exemplary electronic units are described in U.S. Pat. No. 3,857,398, issued to Rubin on Dec. 31, 1974, and U.S. Pat. No. 3,857,399, issued to Zacouto on Dec. 31, 1974.

Catheters of the prior art have included five principal parts: a plug portion for cooperating with the jacks of the electronic unit; two conductors for conducting the electrical signals to and/or from the region of the body to be stimulated or at which naturally produced stimuli are to be sensed; an electrode portion for electrically contacting the region of the body to be sensed and/or stimulated; and an insulation tube connecting the plug and electrode portions and through which the conductors extend.

According to the prior art configuration to which the present invention is most closely related, the plug portion includes a Y-shaped casing made of silicone rubber. Single passages extend through each of the arms of the casing and into the base of the casing. The passages extend parallel to one another through the base of the casing. The plug portion of such a configuration further includes hollow elongate pins extending parallel to one another from the tips of the arms of the casing, the chamber of each pin communicating with the passage through the art from which the pin extends. The pins are of a configuration that will mate with the jacks of the electronic unit.

The conductors of such a prior art configuration are spiralwound wires of highly flexible metal, the winding of the wires being such that adjacent windings are in full contact with one another when at rest and such that a passage extends through the windings. One end of each conductor extends through one of the passages of the plug portion and is electrically connected to the pin of the plug portion communicating with that passage.

The insulation tube of such a configuration includes a bilumen tube of circular cross section. One end of the bilumen tube abuts the tip of the base of the casing of the plug portion such that the passages of the base communicate with the passages of the bilumen tube. The conductors, therefore, extend directly into and through the passage of the bilumen tube.

Figure 2:
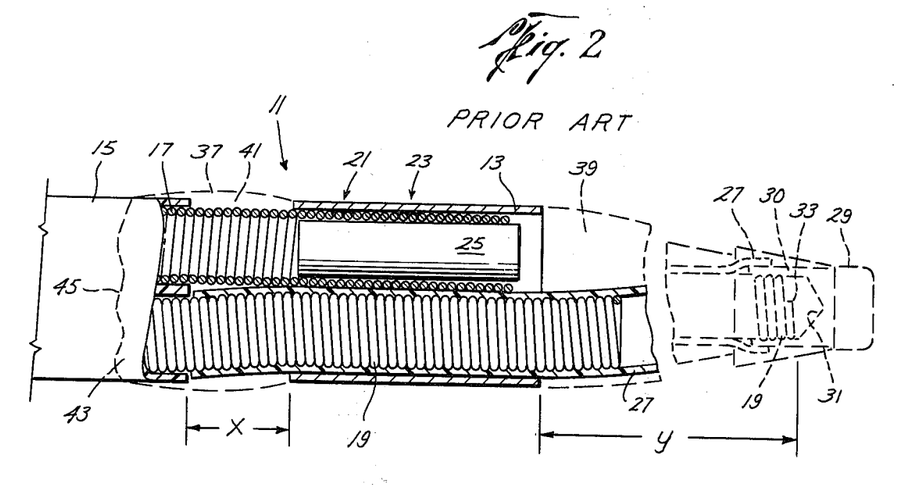
FIG. 2 is a sectional view of the electrode portion of a prior art catheter (previously described)

The electrode portion of such a prior art configuration is shown in FIG. 2 of the drawings. As shown therein, electrode portion 11 includes metallic annular anode ring 13 spaced a distance X from the end of insulation tube 15 opposite the plug portion and having an outer diameter substantially equal to that of tube 15. Conductors 17, 19 extend from the end of tube 15 into ring 13, conductor 17 terminating within ring 13 and conductor 19 passing through the entirety of ring 13 and a distance Y beyond ring 13. Electrode portion 11 further includes resistance weld points 21, 23 electrically connecting and physically securing conductor extension 17 to the inner surface of anode ring 13; cylindrical slug 25 disposed in the passageway of conductor extension 17 for facilitating welding of extension 17 to ring 13; unilumen tube 27 made of silicone rubber abutting tube 15 and through which conductor 19 extends whereby conductor 19 is electrically insulated from extension 17 and ring 13; cathode tip 29 having socket stem 30 and blind socket passage 31 within which extreme end 33 of conductor 19 is secured, unilumen tube 27 being expanded about the outer periphery of stem 30; and silicone rubber potted regions 37, 39. Thus, electrode portion 11 has bipolar spaced electrodes, anode ring 13 being the proximal (nearest the electronic unit) electrode and tip 29 being the distal electrode.

Potted region 37 has major portion 41 extending between ring 13 and tube 15 and filling in the spaces between conductor 17 and unilumen tube 27 and between the ends of unilumen tube 27 and tube 15. Portion 41 has a generally cylindrical outside surface having a diameter slightly greater than that of tube 15. Another portion of potted region 37 extends into ring 13. A third portion 43 of potted region 37 extends over the outside of tube 15 and terminates at feather edge 45.

Potted region 39 surrounds the portion of unilumen tube 27 extending between ring 13 and cathode tip 29 as well as socket step 30 of tip 29. Potted region 39 is vulcanized to ring 13 with a portion of potted region 39 extending into ring 13. The outer surface of potted region 39 adjacent ring 13 is contiguous with the outer surface of ring 13 whereby unilumen tube 27 is asymetrically disposed in potted region 39 adjacent ring 13. The position of tube 27 in potted region 39 is such that tube 27 is coaxial with the outer surface of potted region 39 adjacent tip 29. Thus, the axes of potted region 39 and unilumen tube 27 do not assume the same direction between ring 13 and tip 29.

One or more of the above-described catheter features are disclosed in the following U.S. Patents:

| U.S. Pat. No. | Issued | Inventor |
|---|---|---|
| 3,974,834 | August 17, 1976 | Kane |
| 4,046,151 | September 6, 1977 | Rose |
| 3,769,984 | November 6, 1973 | Muench |
| 3,348,548 | October 24, 1967 | Chardack |
| 4,057,067 | November 8, 1977 | Lajos |
| 4,010,755 | March 8, 1977 | Preston |
| 3,853,398 | December 31, 1974 | Rubin |
| 3,788,329 | January 29, 1974 | Friedman |

All of the above-listed patents show bipolar or dual electrodes for the electrode portion. Chardack, Lajos and Friedman show the use of spiral conductors to give flexibility to the catheter. Muench, Chardack, Preston and Rubin show one conductor passing through a ring shaped electrode and connecting to a tip electrode spaced apart from the ring, and the other conductor terminating at and connecting to the internal surface of the ring electrode. Chardack shows slugs inserted in the ends of the spiral conductors where they are attached to the ring and tip electrodes.

Some variations from the above-described prior art configuration but pertinent to the invention are shown in the above-listed patents. Thus, Muench shows the use of stranded conductors that are attached to the electrode by crimping. Chardack shows the bilumen insulation tube extending into the anode ring. One lumen of the bilumen tube is cut off and the conductor extending through that portion is attached to the internal surface of the ring. The other lumen extends through the ring and to the tip electrode. Silicone rubber is molded about a portion of the tip electrode, about the lumen portion extending to the tip electrode, and within the anode ring such that a portion of the rubber overlaps the bilumen tube within the ring.

Kane, Rose, Chardack and Friedman show Y-shaped plug portions.

Kane and Rose show a bilumen tube with spiral conductors, one conductor extending into the terminating at the anode ring, and the other conductor extending through the ring and terminating in a tip electrode spaced from the anode ring. The latter conductor is potted in silicone rubber.

Various alternative forms of catheters are shown in the following U.S. Patents:

| U.S. Pat. No. | Issued | Inventor |
|---|---|---|
| 3,596,662 | August 3, 1971 | Bolduc |
| 3,844,292 | October 29, 1974 | Bolduc |
| 3,875,947 | April 8, 1975 | Jula |
| 3,888,260 | June 10, 1975 | Fischell |
| 4,010,758 | March 8, 1977 | Rochland |
| 4,033,355 | July 5, 1977 | Amundson |

Bolduc '662 is of interest showing molding equipment. Bolduc '292 shows an electrode with a spear point such as that shown in FIG. 2.

A problem encountered in the use of catheters of the abovedescribed prior art configuration is a tendency of various connections in the electrode portion and the junction of the insulation tube and electrode portion including metal-to-metal connections, rubber-to-rubber connections and metal-to-rubber connections, to fail. Failure occurs in the light of constant movement of the body, including involuntary movement of internal organs, that causes shear and stres forces to be applied to the electrode portion and the junction of the electrode portion and insulation tube. Such failures often result in body fluid leakage all the way to one or both of the conductors causing an undesirable change in system sensitivity. Furthermore, a short circuit may be caused between the conductors or the connection of a conductor to its corresponding electrode may be opened.

Another problem persisting in the prior art catheters of the type described has been a tendency of the tube extending between the ring electrode and the tip electrode to twist whereby proper insertion of the electrode portion is sometimes hampered.

SUMMARY OF THE INVENTION

The present invention provides a catheter having a bipolar spaced electrodes wherein the connections and junctions in and adjacent the electrode portion, including rubber-to-rubber, rubber-to-metal, and metal-to-metal connections, have very little potential for failing even in view of rigorous forces that may be applied by body and internal organ movement. Furthermore, the present invention provides a catheter having spaced ring and tip electrodes wherein the tube leading from the ring to the tip has essentially no tendency to twist.

The present invention provides an electrode assembly for a cathether having first and second conductors, comprising an anode ring having a longitudinal axis, a proximal end and a distal end, and including an outer portion and an inner portion connected to the outer portion. The inner anode ring portion includes a solid member having a blind passage therein and a channel therethrough. One end of the first conductor is received in the blind passage and retained therein by a pair of crimps impressed into the solid member against the conductor end. The second conductor extends through the anode ring in the channel. Alternatively, the inner anode ring portion includes a post which is received in a passage in the end of the first conductor and is welded to the first conductor. The second conductor includes a lead portion and a tip portion spaced from the lead portion, and the anode ring includes a feed-through tube extending therethrough and interconnecting the lead portion and the tip portion of the second conductor.

The outer anode ring portion includes a tubular part having a wall with an outer surface and an inner surface, and including an aperture extending through the wall from its outer surface to its inner surface. Some portions of the inner surfaces, or the inner and outer surfaces, of the outer anode ring portion including the tubular part are roughened.

The outer anode ring portion at the distal end of the anode ring includes a ring tip having a passage therethrough, such passage through such ring tip being coaxial with the anode ring and carrying such second conductor therewithin.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

1. General Description: Electronic Unit, Insulation Tube and Conductors

Figures 1, 1A:
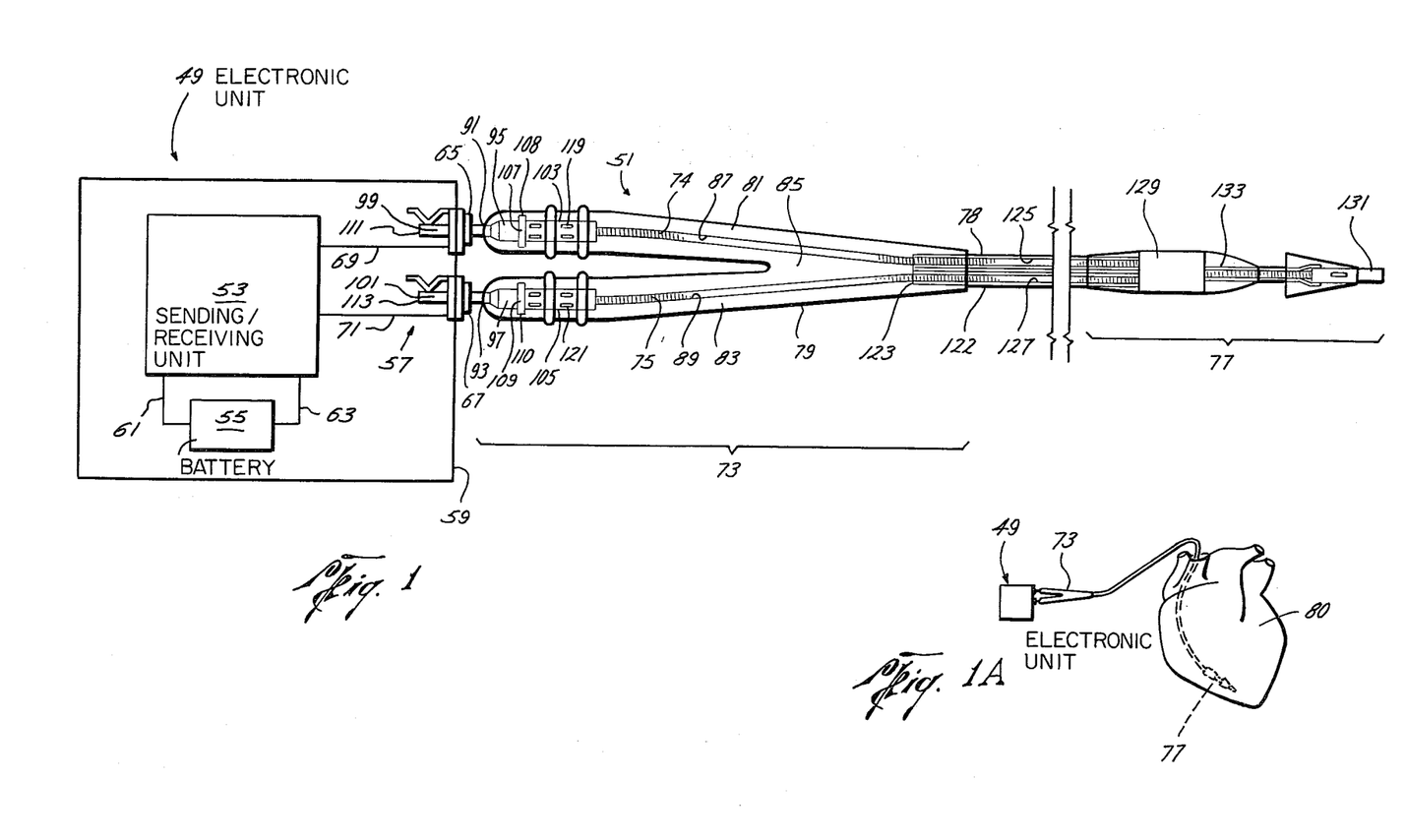
FIG. 1 is a partially schematic, partially enlarged planar representation of a catheter of the type incorporating the invention.
FIG. 1A is a partially schematic, partially pictorial representation of the general use of a catheter of the type incorporating the invention.

In FIGS. 1 and 1A, there is shown a system for use in transmitting electrical signals to and from various internal regions of an animal's body. For example, FIG. 1A illustrates the use of such a system in connection with a heart. The system shown in FIGS. 1 and 1A includes electronic unit 49 and catheter 51.

Electronic unit 49, shown largely schematically, has electronic circuit 53 for sensing the existence or non-existence of body produced electrical stimuli and/or for providing artificial electrical stimuli (an exemplary circuit is described in U.S. Pat. No. 3,857,399, issued to Zacouto on Dec. 31, 1974); battery 55 for powering electronic circuit 53; connector device 57 for connecting electronic circuit 53 to catheter 51; and casing 59 enclosing batter 55 and electronic circuit 53. Battery 55 is electrically connected to electronic circuit 53 by conductors 61, 63. Connector device 57 includes jacks 65, 67 attached to casing 59 such that they are parallel to one another and such that their respective receptacles face outwardly from casing 59. Jacks 65, 67 are connected to electronic circuit 53 by conductors 69, 71, respectively.

Catheter 51 includes plug portion 73 for cooperating with connector device 57 of electronic unit 49; conductors 74, 75 for conducting electrical signals to and/or from the region of the body to be stimulated or at which naturally produced stimuli are to be sensed; electrode portion 77 for electrically contacting the region of the body to be sensed and/or stimulated; and insulation tube 78 connecting plug portion 73 to electrode portion 77 and through which conductors 74, 75 extend. In use, electrode portion 77 of catheter 51 may be embedded directly in the tissue of the body region to be sensed and/or stimulated, for example as in FIG. 1A, where electrode portion 77 is embedded in a wall of heart 80.

Plug portion 73 includes Y-shaped casing 79 having arms 81, 83 and base 85. Single passages 87, 89 extend through the entire lengths of arms 81, 83, respectively, and continue through the entire length of base 85. Arm 81 includes opening 91 at its tip communicating with passage 87. Arm 83 includes opening 93 at its tip and communicating with passage 89.

Casing 79 is made of a material that is somewhat flexible, but sufficiently firm to maintain the casing in a predetermined shape when no substantial external force is applied, and that is substantially inert to body fluids. A silicone rubber, such as that sold under the trademark Silastic, is preferred. The flexibility of the silicone rubber casing is dependent upon the thickness of the wall of the casing; i.e., the distance between the periphery of the casing and a passage extending therethrough. Flexibility is increased as thickness is decreased. A preferred thickness giving the desired flexibility is 0.100 inch.

Plug portion 73 further includes hollow, elongate pin plugs 95, 97 having mating ends 99, 101, respectively, and base ends 103, 105, respectively. Base ends 103, 105 extend through openings 91, 93, respectively, and into passages 87, 89, respectively. Base ends 103, 105 have respective outwardly extending circumferential flanges 107, 109 fixed thereon, said flanges being received in respective annular grooves 108, 110 around the inner surface of passages 87, 89, whereby said base ends are retained in said passages. Mating ends 99, 101 have a configuration by which they can be mated securely with jackets 65, 67 of electronic unit 49. The connection between the jacks and the pin plugs is of a hermitc nature, impervious to body fluid intrusion as far as possible under present technology, as is the seal around the plugs at the tips of arms 81, 83. The extreme tips of mating ends 99, 101 have openings 111, 113, respectively, communicating with the chambers (not shown) extending through pin plugs 95, 97. The chambers of pin plugs 95, 97 are coaxial with and communicate with passages 87, 89, respectively.

Conductors 74, 75 comprise wires that have been wound in as tight a spiral as possible, that is to say, with little or no space between adjacent windings. Preferably, conductors 74, 75 are formed from 0.010 inch diameter wire made of strainless steel, e.g. "Elgiloy," a trademark of Eligloy Co., division of American Gage and Machine Co., subsidiary of Katy Industries, Inc.; and the spiral has an inside diameter of 0.016 inch and an outside diameter of 0.036 inch.

Conductors 74, 75 extend through passages 85, 87, respectively, and are secured therein such that conductors 74, 75 are in permanent electrical contact with base ends 103, and 105 of pin plugs 95, 97, respectively. Such permanent electrical contact may be effected by attaching conductors 74, 75 to base ends 103, 105 by crimping, as at 119, 121, respectively.

Insulation tube 78 includes bilumen tube 122 having passages 125, 127 therethrough. Bilumen tube 122 has proximal end 123 enclosed within the tip of base 85 of casing 79 of plug portion 73 such that passages 125, 127 are in communication with passages 87, 89, respectively, of casing 79. Conductors 74, 75 extend from passages 87, 89, respectively, and into and through the length of passages 125, 127, respectively, of bilumen tube 122. Bilumen tube 122 should be securely connected to casing 79, the connection being of a hermetic nature and impervious to fluid intrusion as far as possible under present technology, the method of connection depending upon the materials from which tube 122 and casing 79 are made. Tube 122 should be made of a highly flexible material that is substantially inert to body fluids. Preferably, tube 122, like casing 79, is made of silicone rubber such as that sold under the trademark Silastic. The wall thickness of tube 122 should be substantially smaller than that of casing 79 so as to provide tube 122 with greater flexibility. The preferred wall thickness (maximum) of tube 122 is approximately 0.020 inch. When both casing 79 and tube 122 are made of silicone rubber, as preferred, they may be connected together by vulcanization.

Electrode portion 77 of catheter 51 includes anode ring 129 and cathode tip 131, cathode tip 131 being spaced distally from ring 129 with cathode tube 133 disposed therebetween. Conductor 74 extends from tube 78 and is secured to the inner surface of ring 129. Conductor 75 extends through cathode tube 133 and is connected to cathode tip 131.

The present invention includes several embodiments of electrode portion 77, all of which are in conformity with the general description set forth above. The details of these embodiments are set forth below. The configuration of the distal end of insulation tube 78 and the connection of tube 78 to electrode portion 77 vary according to the particular embodiment of electrode portion 77 and will be discussed separately with respect to each particular embodiment of electrode portion 77.

2. Anode Insert Embodiment a. Configuration

Figure 3:
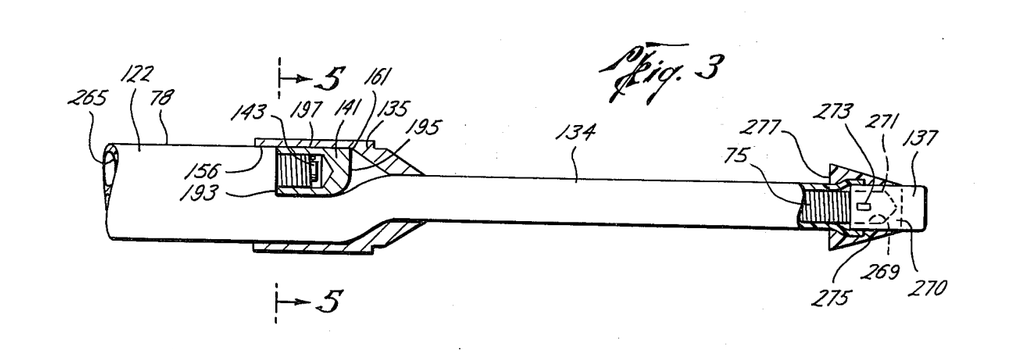
FIG. 3 is an enlarged sectional view of the electrode portion of a first embodiment of the invention.
Figure 4:
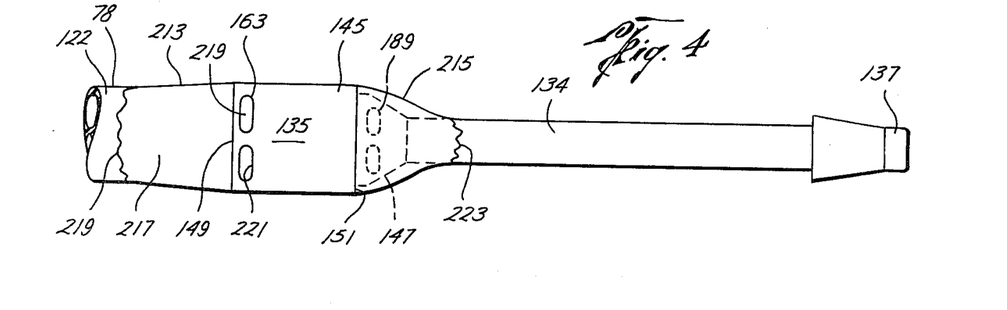
FIG. 4 is an enlarged planar view of the electrode portion of the first embodiment of the invention.
Figures 5, 6:
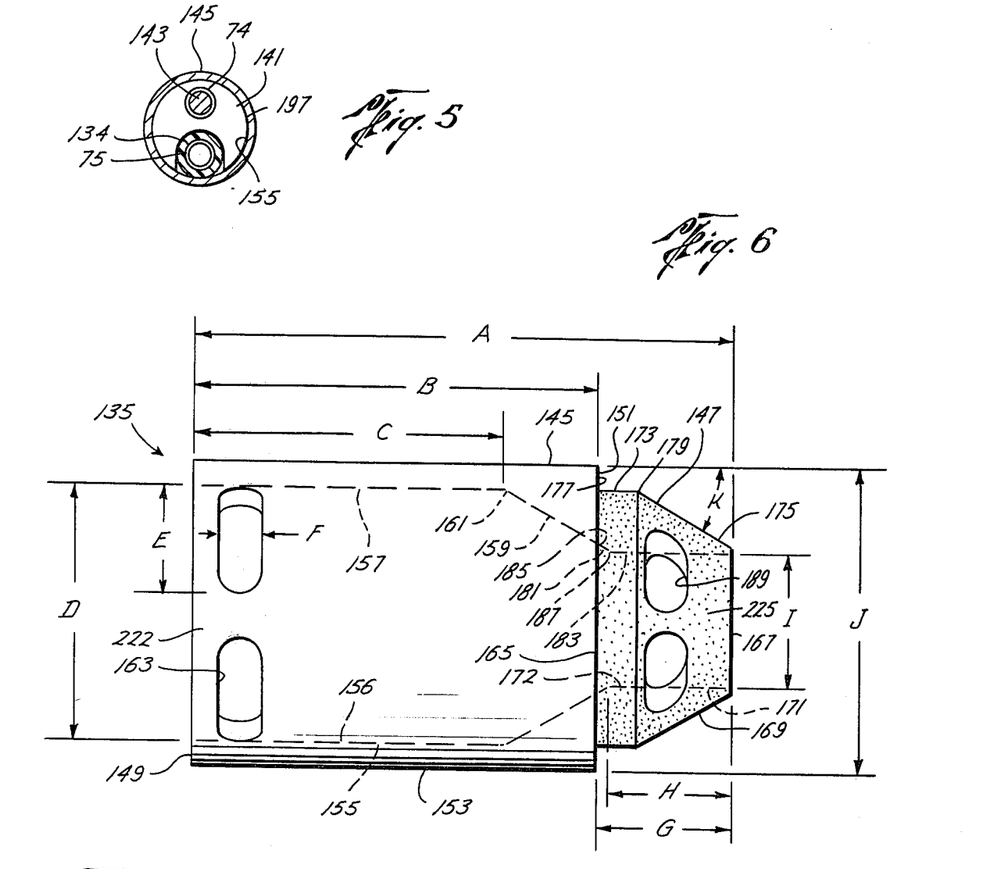
FIG. 5 is a sectional view taken along 5—5 of FIG. 3.
FIG. 6 is a detailed, enlarged planar view of the anode ring of the first embodiment of the invention.

The configuration of the first embodiment of the electrode portion of the invention, or the anode insert embodiment, is shown in FIGS. 3, 4 and 5. FIGS. 6, 7, 8 and 9 show component parts of the anode insert embodiment of the electrode portion of the invention as they exist prior to assembly. Assembly of the component parts, which is described infra under part b, includes the operations of crimping certain components and force-fitting others together; as a result, the assembled components may have a configuration that is somewhat distorted from that shown and described. Because such distortion is not predictable and will vary from one assembly to the next, and because an understanding of the distortion is not necessary to an understanding of the invention or to making, using or otherwise practicing the invention, the description and drawings set forth only the undistorted configurations of the component parts.

Figures 9, 10:
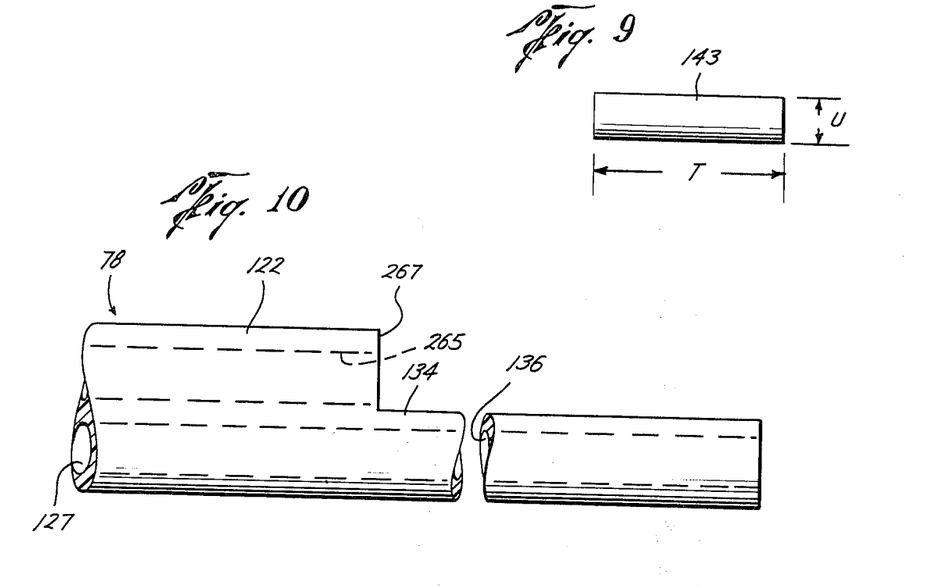
FIG. 9 is an enlarged view of the slug of the first embodiment of the invention.
FIG. 10 is an enlarged, planar view of the bilumen-unilumen tube of the electrode portion of the first embodiment of the invention.

When the anode insert embodiment of the invention is employed, the distal end of insulation tube 78 has the configuration shown in FIG. 10. Referring to FIG. 10, tube 78 further includes unilumen tube 134 having passage 136 integrally connected to bilumen tube 122 such that passage 136 is coaxial with passage 127 of bilumen tube 122. Unilumen tube 134 is made of the same material as bilumen tube 122 and, if made of silicone rubber, can be extruded along with bilumen tube 122. Alternatively, a vulcanized unilumen tube 134 can be molded on to bilumen tube 122. Unilumen tube 134 should have a uniform wall thickness, preferably about 0.012 inch, with passage 136 having a diameter substantially equal to that of passage 127.

The anode insert embodiment of the electrode portion of the invention includes several component parts cooperating with the distal end of insulation tube 78, as just described, and with conductors 74, 75 extending through and from tube 78. Referring to FIGS. 3 and 4, the component parts include anode ring 135, cathode tip 137, insert 141 and slug 143.

Referring particularly to FIG. 6, anode ring 135 is an integral unit that includes ring body 145 and ring tip 147.

Ring body 145 has a generally cylindrical configuration and has proximal end 149, distal end 151, outer surface 153 and inner surface 155, inner surface 155 defining passage 156. Outer surface 153 is of constant diameter along its length. Inner surface 155 includes cylindrical portion 157 and conical portion 159. Cylindrical portion 157 is of constant diameter and extends from proximal end 149 through the majority of the length of ring body 145. Conical portion 159 extends from the distal end of cylindrical portion 157, that is, the end of cylindrical portion 157 opposite proximal end 149, to distal end 151 of ring body 145. The diameter of conical portion 159 is equal to that of cylindrical portion 157 at junction 161 of conical portion 159 and cylindrical portion 157 and decreases linearly moving away from junction 161. Ring body 145 further has circumferentially spaced apertures 163 spaced slightly from proximal end 149. Apertures 163 extend through ring body 145 from outer surface 153 to inner surface 155. As shown, apertures 163 may have a slot-like configuration in which the magnitude of the dimension of the aperture moving in the direction of the axis of ring body 145 is substantially less than the magnitude of the dimension moving circumferentially. Alternatively, apertures 163 may have a generaly circular, rectangular or any poly-lateral configuration.

Ring tip 147 has proximal end 165, distal end 167, outer surface 169 and inner surface 171, inner surface 171 defining passage 172. Ring tip 147 is coaxially and integrally connected to ring body 145 with proximal end 165 of ring tip 147 adjoining distal end 151 of ring body 145. Outer surface 169 of ring tip 147 has cylindrical portion 173 and conical portion 175. Cylindrical portion 173 extends from proximal end 165 of ring tip 147 through a portion of the length of ring tip 147 and conical portion 175 extends through the remainder of the length of ring tip 147 to distal end 167 of ring tip 147. Cylindrical portion 173 has a constant diameter less than that of outer surfaces 153 of ring body 145 whereby there is an annular shoulder 177 at distal end 151 of ring body 145 extending between outer surface 153 of ring body 145 and outer surface 169 of ring tip 147. Conical portion 175 has a diameter equal to that of cylindrical portion 173 at junction 179 of cylindrical portion 173 and conical portion 175. The diameter of conical portion 175 decreases linearly from junction 179 to distal end 167 of ring tip 147.

Inner surface 171 of ring tip 147 includes conical portion 181 and cylindrical portion 183. Conical portion 181 is an extension of conical portion 159 of ring body 145. Thus, conical portion 181 extends from its junction 187 with cylindrical portion 183 to its intersection 185 with the plane of proximal end 165 of ring tip 147, from where conical portion 159 continues. Because ring tip 147 is integrally connected to ring body 145 and because conical portion 181 is an extension of conical portion 159, there is no physical evidence of intersection 185. That is, the conical surface 181, 159 is smooth and continuous. Cylindrical portion 183 has a constant diameter equal to the diameter of conical portion 181 at junction 187.

As shown in FIG. 6, the length of conical portion 175 of outer surface 169, the rate at which the diameter of conical portion 175 decreases moving toward distal end 167 of ring tip 147, and the diameter of cylindrical portion 183 of inner surface 171 relate to one another such that the diameter of conical portion 175 is slightly greater than the diameter of cylindrical portion 183 at distal end 167 of ring tip 147, e.g. 0.020 inches greater.

Ring tip 147 further includes apertures 189 substantially equally spaced about a circumference near the center of ring tip 147, apertures 189 extending from outer surface 169 to inner surface 171. As with apertures 163, aperturs 189 may have either a slot-like, circular, rectangular or any other polylateral configuration.

As shown in FIG. 3, insert 141 has a generally cylindrical body and has proximal end 193, distal end 195 and outer surface 197. Insert 141 is disposed in passage 156 of anode ring 135 such that distal end 195 is aligned with junction 161. The length of insert 141 is substantially shorter than the length of cylindrical portion 57 of inner surface 155 of ring body 145 such that no portion of insert 141 covers any portion of apertures 163. The outer diameter of insert 141 prior to insertion of insert 141 into passage 156 (as described infra) is slightly larger than the diameter of cylindrical portion 57 prior to such insertion such that insert 141 is rigidly held within passage 156 by an interference fit and such that all of outer surface 197 of insert 141 is in full contact with a portion of inner surface 155 of ring body 145.

Figure 7:
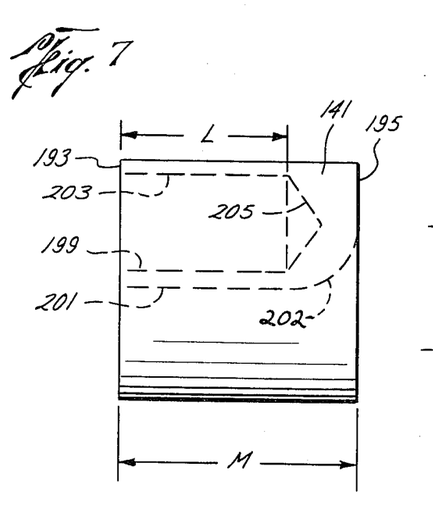
FIG. 7 is a detailed, enlarged planar view of the insert of the first embodiment of the invention.
Figure 8:
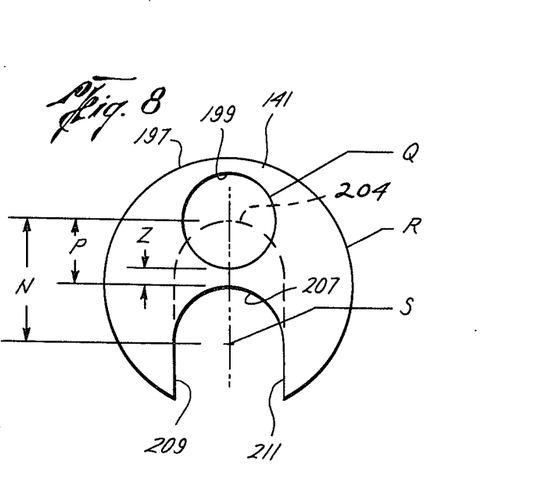
FIG. 8 is a detailed, enlarged axial view of the insert of the first embodiment of the invention.

Referring particularly to FIGS. 7 and 8, insert 141 further has blind passage 199 and channel 201. Blind passage 199 extends from proximal end 193 of insert 141 through most, but not all, of the length of insert 141 in a direction parallel to the axis of insert 141. Passage 199 includes cylindrical portion 203 and conical portion 205. Cylindrical portion 203 has a diameter slightly greater than the diameter of conductor 74. The axis of passage 199 is spaced from the axis of insert 141 a distance greater than the radius of cylindrical portion 203 so that there is a distance Z between the surface of cylindrical portion 203 and the axis of insert 141. Conical portion 205 is formed when passage 199 is drilled.

Channel 201 extends through the entire length of insert 141 and has a straight, proximal portion extending from end 193 of insert 141 a distance substantially equal to the length of cylindrical portion 203 of blind passage 199, in a direction parallel to the axis of insert 141; and a saddle-shaped distal portion 202 extending the rest of the way through insert 141 to end 195. Saddle shaped portion 202 curves upwardly, i.e. toward the axis of blind passage 199, to provide a guide for the orientation of tube 134 toward the axis of anode ring 135 (see FIG. 3). Referring particularly to FIG. 8, the streight, proximal portion of channel 201 has semicylindrical portion 207 and sidewall portions 209, 211. Semicylindrical portion 207 has a radius substantially larger than that of conductor 75. The axis of semicylindrical portion 207 is spaced from the axis of insert 141 a distance substantially equal to the radius of semicylindrical portion 207. The axis of semicylindrical portion 207 is aligned with the axes of passage 199 and insert 141, i.e., a line passing through the axis of semicylindrical portion 207 and the axis of passage 199 also passes through the axis of insert 141. Sidewall portions 209, 211 are in planes parallel to one another and tangent to opposite sides of semicylindrical portion 207 and extend from semicylindrical portion 207 to outer surface 197 of insert 141. The upper part of saddle-shaped portion 202 is semicircular in cross section and has a radius the same as that of semicylindrical portion 207, and the lower part of saddle-shaped portion 202 has parallel side walls integral and coplanar with sidewall portions 209, 211. The top 204 of saddle-shaped portion 202 intersects end 195 of insert 141 approximately the same distance from the axis of insert 141 as is the axis of blind passage 199.

Referring particularly to FIG. 9, slug 143 is shown in side elevation. Slug 143 comprises an elongate piece of solid metal having a generally right circular cylindrical shape. Slug 143 has a diameter slightly smaller than the inside diameter of conductor 74. Slug 143 is preferably made from a metal such as, for example, stainless steel, e.g. "Elgiloy", or other body-implantable metal such as platinum or platinum-iridium or gold alloy.

As noted previously, the components of the anode insert embodiment of the invention shown in FIGS. 6, 7, 8, and 9 are subject to unpredictable distortion when assembled. However, various dimensions of such components prior to their assembly may be set out to facilitate an understanding of the assembly procedure, described infra in part b. Thus, some of the dimensions of anode ring 135 are designated in FIG. 6 as follows: the letter A is the length of the anode ring from proximal end 149 of ring body 145 to distal end 167 of ring tip 147; B is the length of ring body 145 from its proximal end 149 to its distal end 151; C is the length of cylindrical portion 157 of ring body 145 from proximal end 149 of ring body 145 to junction 161; D is the diameter of passage 156 of ring body 145; E is the extent of apertures 163 measured in a direction circumferential to ring body 145; F is the extent of apertures 163 measured in a direction longitudinally axial to ring body 145; G is the length of ring tip 147 from its proximal end 165 to its distal end 167; H is the length of cylindrical portion 183 of passage 172 from junction 187 to distal end 167; I is the diameter of passage 172; J is the outer diameter of ring body 145; and K is the angle between conical portion 175 of ring tip 147 and outer surface 153 of ring body 145.

Some of the dimensions of the anode insert 141 are designated in FIGS. 7 and 8 as follows: the letter L is the length of the cylindrical portion 203 of blind passage 199; M is the length of the insert 141 from its proximal end 193 to its distal end 195; N is the distance from the axis of passage 199 to the axis of semicylindrical portion 207 of channel 201; P is the distance from the axis of passage 199 to the axis of insert 141; Q is the diameter of passage 199; R is the diameter of insert 141; S is the diameter of semicylindrical portion 207 of channel 201.

Some of the dimensions of slug 143 are shown in FIG. 9 as follows: the letter T is the length of slug 143 along its longitudinal axis; U is the diameter of slug 143.

In a preferred structure of the anode insert embodiment of the invention, the above-described dimensions may have, for example, the following values:

| Dimension | Value |
|---|---|
| Anode Ring | |
| A | .225 Inch |
| B | .170 " |
| C | .130 " |
| D | .124 " |
| E | .044 " |
| F | .020 " |
| G | .055 " |
| H | .050 " |
| I | .060 " |
| J | .145 " |
| K (angle) | 30 degrees |
| Anode Insert | Value (Inches) |
| L | .070 |
| M | .100 |
| N | .052 |
| P | .026 ± .022 |
| Q | .040 |
| R | .125 |
| S | .060 |
| Slug | Value (Inches) |
| T | .080 ± .005 |
| U | .019 |

As shown in FIG. 4, the anode insert embodiment of the invention includes potted regions 213, 215, preferably of silicone rubber, extending away from opposite ends of the anode ring 135 and surrounding portions of tubes 78, 134, respectively. Potted region 213 includes a first portion 217 abutting proximal end 149 of ring body 145 and extending therefrom around insulation tube 78 until terminating in a feathered edge 219. The outer diameters of first portion 217 of potted region 213 and ring body 145 are substantially the same at their interface; the outer diameter of first portion 217 then gradually decreases or tapers moving away from such interface until it is substantially the same as the outer diameter of tube 78 at feathered edge 219.

Potted region 213 also includes a second portion 219 integral with first portion 217 and extending therefrom into passage 156 of ring body 145 around insulation tube 78. Second portion 219 of potted region 213 extends into passage 156 at least as far as distal edges 221 of apertures 163 and fills apertures 163 up to and flush with the outer surface 153 of ring body 145, thus forming a smooth, continuous cylindrical outer surface for ring body 145. Second portion 219 also fills any spaces between insulation tube 78 and inner surface 155 of ring body 145, and between tube 78 and proximal end 193 of insert 141. In order to promote adhesion between the rubber of second portion 219 of potted region 213 and the inner surface 155 of ring body 145, inner surface 155 is roughened by chemical etching or blasting or other process near proximal end 149, e.g. at 222 in FIG. 6.

Potted region 215 at one of its end abuts distal end 151 of anode ring 145, and from there extends so as to surround both ring tip 147 and a portion of that part of unilumen tube 134 which leads from ring tip 147 to cathode tip 137. Potted region 215 terminates at its other end in a feathered edge 223. The outer diameters of potted region 215 and ring body 145 are substantially the same at their interface; the outer diameter of potted region 215 then decreases or tapers moving away from such interface until it is substantially the same as the outer diameter of tube 134 at feathered edge 223. The taper of potted region 215, while less gradual than that of potted region 213, is sufficiently gradual to provide a smooth, continuous transitional surface between the outer surface of unilumen tube 134 and the outer surfaces of anode ring 135, particularly outer surfaces 169, 153 of ring tip 147 and ring body 145, respectively.

Potted region 215 also extends through apertures 189 and into passage 172 of ring tip 147, entirely filling apertures 189 from the outer surface 169 to the inner surface 171 of ring tip 147 and adjoining unilumen tube 134 in passage 172. In order to promote adhesion between the rubber of potted region 215 and the outer surface 169 of ring tip 147, outer surface 169 is roughened as shown at 225 in FIG. 6 in like manner as inner surface 155 of ring body 45. Also, the extended length of ring tip 147 provides sufficient outer surface area to which the rubber may adhere to promote a strong bond.

In the preferred structure of the first embodiment of the invention with tubes 78, 134 and potted regions 213, 215 all made of silicone rubber, potted regions 213, 215 are vulcanized or molded onto and around the respective tubes 78, 134 so as to be integral therewith, both inside and outside anode ring 135. Also, potted regions 213, 215 are vulcanized or molded within or through apertures 163, 189 and onto or around the respective portions of the ring body 145, insert 141 and ring tip 147 as previously described. Thus, a firm, anchored, separation-resistant adhesive connection is provided between tube 78 and anode ring 135, and between tube 134 and anode ring 135.

As shown in FIG. 5 and as noted supra, when insert 141 is positioned in passage 156 of anode ring 135 there is full contact between outer surface 197 of insert 141 and inner surface 155 of ring body 145, except for that portion of insert 141 between sidewall portions 209, 211 corresponding to channel 201.

Insert 141 and ring body 145, like all metal parts described herein, are preferably made from a body-compatible metal such as, for example, platinum, platinum-iridium, gold alloy or stainless steel. When such a metal is used, there will be a substantially complete, body fluid-resistant electrical contact between the insert 141 and the ring body 145. As will be described infra under part b, conductor 74 is crimped into full electrical contact with insert 141, hence, is also placed in full electrical contact with ring body 145.

Since rubber tube 134 occupies channel 201 with a wall of tube 134 being disposed between conductor 75 and ring body 145, it will be appreciated that conductor 75 is electrically insulated from ring body 145. Also, since rubber tube 134 passes entirely through the anode ring 135 including the ring tip 147 with conductor 75 therewithin, conductor 75 is completely electrically insulated from the entire anode ring 135.

B. Assembly

FIGS. 11, 12, 13 and 14 illustrate some of the steps in the assembly of the anode insert embodiment of the invention. As part of such assembly, the conductor 74 must be securely connected to the anode insert 141.

Figures 11, 12, 13:
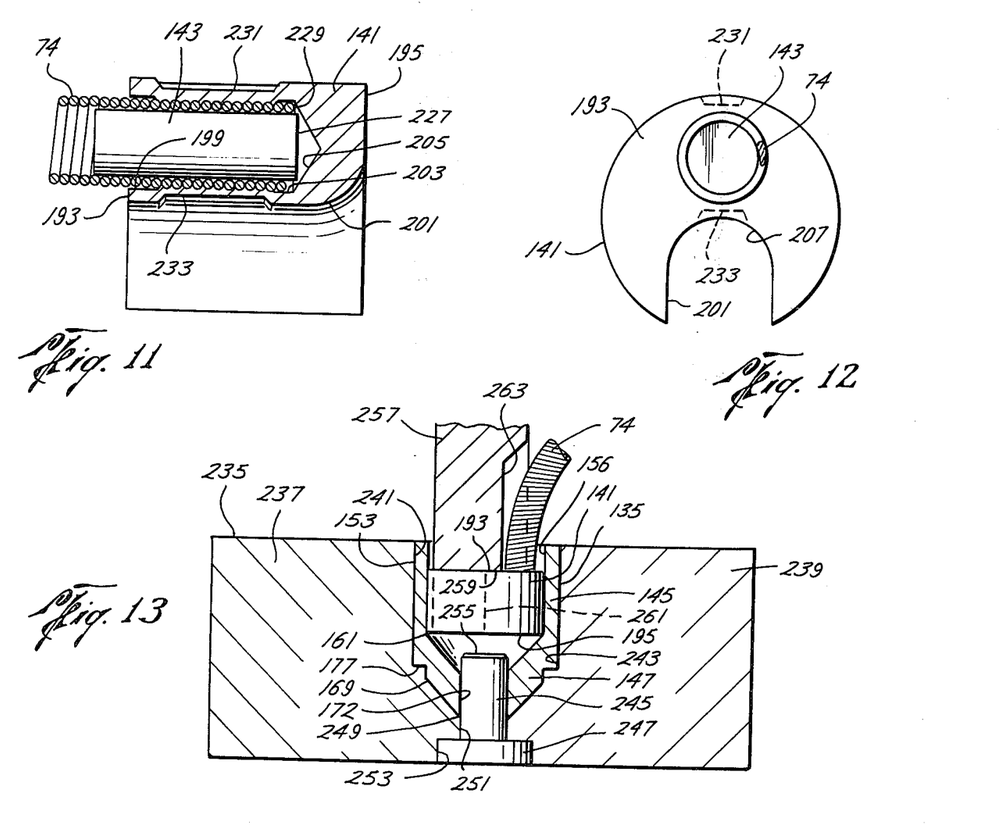
FIG. 11 is an enlarged, sectional view of the insert of the first embodiment of the invention with the conductor extension crimped in place.
FIG. 12 is an enlarged, end view of the insert of the first embodiment of the invention with the conductor extension crimped in place.
FIG. 13 is a sectional view of a portion of the electrode portion of the first embodiment of the invention illustrating a step in the method of assembling the electrode portion of the invention.

Such a connection is obtained by crimping the insert 141 and the conductor 74 together.

Referring to FIGS. 11 and 12, the crimped connection between insert 141 and conductor 74 is shown in longitudinal section and in proximal end elevation, respectively. Prior to crimping, slug 143 is inserted into the passage in conductor 74 such that its distal end 227 is flush with, or protrudes only slightly from, the distal end 229 of coil conductor 74. Distal end 229 of coil conductor 74 with the inserted slug 143 is then inserted into blind passage 199 of insert 141 until end 229 abuts conical portion 205 of passage 199 and the coil conductor and slug occupy substantially the entire cylindrical portion 203 of passage 199.

With the coil conductor 74 and its inserted slug 143 in place in passage 199 of insert 141, two elongate trapezoidal crimps 231, 233 are impressed into insert 141 on opposite sides of the coil conductor. Crimp 233 is impressed into the wall of semicylindrical portion 207 of channel 201 below the coil conductor, and crimp 231 is impressed into the outer surface 197 of insert 141 above the coil conductor and opposite crimp 233. The longitudinal axes of crimps 231, 233 are aligned with the axes of semicylindrical portion 207, passage 199 and insert 141.

Slug 143 provides solidity and rigidity for the coil conductor end so that it may be pinched between crimps 231, 233 with sufficient pressure and friction so as to obtain a reliable mechanical and electrical connection between the coil conductor 74 and the insert 141.

Prior to crimping, the slug 143 fits snugly within the passage of the coil conductor 74, and the coil conductor 74 in turn fits snugly within the passage 199 of insert 141. Then, with the dimensions of the components having the values shown in the tables set out previously, crimps 231, 233 each may be 0.060 inch long, 0.020 inch wide at the outermost or widest part, and 0.003 inch deep.

The tensile strength of the crimped connection should exceed five pounds or the tensile strength of conductor 74, whichever is greater. It is preferred that the crimps 231, 233 have a trapezoidal shape, in order to increase the strength and reliability of the crimped connection. Note that in prior art assemblies the conductor is welded to the anode, see FIG. 2 at 21, 23; crimping rather than welding eliminates the brittleness and reduction of tensile strength at the weld zone that come with the old welding technique.

After the coil conductor 74 is securely crimped to insert 141, insert 141 is securely connected to anode ring 135. This is accomplished by driving insert 141 into passage 156 of anode ring 135. Examination of the outer diameter of insert 141 (FIG. 8, at R) and the diameter of passage 156 (FIG. 6, at D) reveals that a 0.001 inch interference exists between the two (see tables of preferred dimensions, supra). In order to press the insert 141 into passage 156 of anode ring 135, the drive fit fixture and driving pin shown in FIG. 13 must be used.

Referring to FIG. 13, the drive fit fixture includes a split cavity vise 235 having a pair of jaws 237, 239 that may be opened or closed about the anode ring 135 for alternately releasing or holding ring 135. Jaws 237, 239 have depressions 241, 243, respectively, cut into their opposing faces with each depression having an upper portion with dimensions machined exactly to those of a longitudinal half of anode ring 135, such that when the jaws are in closed position the upper portion of depressions 241, 243 fit together to form a cavity having dimensions corresponding exactly to the dimensions of outer surfaces 153, 169 and 177 of anode ring 135.

The drive fit fixture also includes a centering pin 245 attached to a disc shaped base 247. Pin 245 is cylindrical and has a diameter slightly less than the diameter of the passage 172 in ring tip 147 (FIG. 6, at I). When the jaws 237, 239 are in closed position forming the anode ring-shaped cavity, pin 245 extends vertically upward through an aperture 249 in the bottom of the cavity such that pin 245 is coaxial with and centered within such cavity. The lower portions of depressions 241, 243 below aperture 249 have semicylindrical walls as at 251, 253 with dimensions machined exactly to those of pin 245 and base 247, respectively, in like manner as the upper portions of the depressions are machined to the dimensions of the anode ring.

Prior to driving the anode insert 141 into the anode ring 135, the anode ring is placed in the vise 235 and the jaws 237, 239 are closed about the anode ring such that the anode ring fits snugly within the cavity formed by depressions 241, 243. Centering pin 245 is inserted through aperture 249 and into the anode ring through passage 172 in ring tip 147. Centering pin 245 extends through passage 172, beyond the proximal end 165 of ring tip 147 and into passage 156 of ring body 145, but not as far as junction 161 between cylindrical portion 157 and conical portion 159 of passage 156. That is, end 255 of pin 245 is disposed between the proximal end 165 of ring tip 147 and the junction 161.

With the anode ring 135 centered and held in place by jaws 237, 239 and pin 245, the anode insert 141 with the attached coil conductor 74 may be driven into it. In order to drive the insert 141 into the ring 135, the insert is placed on the tip of a driving pin 257. Driving pin 257 includes on its tip a driving portion 259 that abuts proximal end 193 of insert 141 and a stabilizing portion 261 that extends into and fits snugly within channel 201. There is also provided a coil conductor clearance cavity 263 that receives a portion of coil conductor 74 to allow driving portion 259 of pin 257 to extend partially around the coil conductor, thereby increasing the area of contact between such driving portion and proximal end 193 of insert 141.

When the anode insert 141 is placed on the tip of the driving pin 257 it is held there partly by friction between stabilizing portion 261 and the walls of channel 201. The tip of the driving pin 257 carrying the insert 141 is then aligned with passage 156 in ring body 145, and sufficient downward axial force is applied to the driving pin to drive it and the insert 141 into the ring body. The insert is driven into the ring body until distal end 195 of insert 141 reaches junction 161 at the end of cylindrical portion 157 of passage 156. The driving pin 257 is then withdrawn from the insert 141 and the ring 135.

Figure 14:
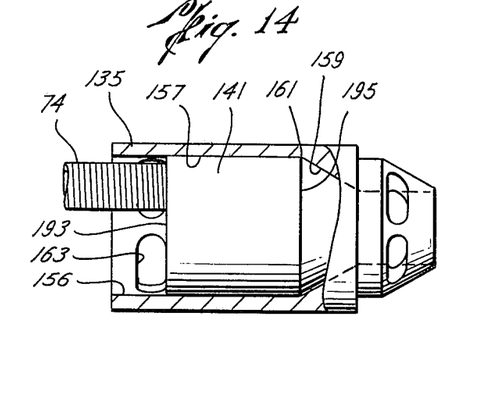
FIG. 14 is an enlarged, partially sectional view of a portion of the electrode portion of the first embodiment of the invention illustrating a step in the method of assembling the electrode portion of the invention.
Figure 15:
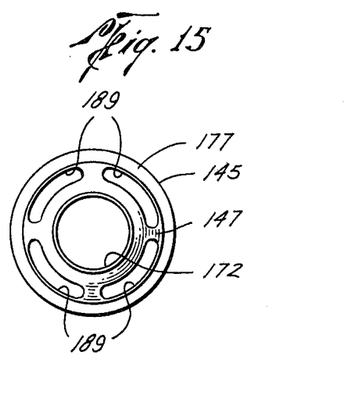
FIG. 15 is an enlarged, end view of the anode ring of the electrode portion of the first embodiment of the invention.

The position of the anode insert 141 in the anode ring is shown in FIG. 14. Referring to that figure, distal end 195 of insert 141 abuts the shoulder at junction 161 created by conical portion 159 of passage 156. Proximal end 193 of insert 141 is flush with distal edges 221 (FIG. 4) of apertures 163.

The friction and pressure between the inner surface 155 of ring body 145 and the outer surface 197 of anode insert 141 results in a firm, strong and reliable mechanical and electrical connection between insert 141 and anode ring 135. In a press fit of this type, using as contacting surfaces the generally cylindrical surfaces of the anode insert and the anode ring, which are large as compared to the overall size of the components, the asperities common to metal surfaces are overcome and maximum load bearing contact is achieved. Also, since coil conductor 74 is securely mechanically and electrically connected to insert 141, a secure and reliable electrical connection exists in turn between coil conductor 74 and anode ring 135.

With the insert 141 securely connected to the anode ring 135, the remainder of the assembly of the anode insert embodiment of the electrode portion of the invention may proceed. Thus, the free end of unilumen tube 134 is inserted and pulled through the anode ring 135 by threading it through channel 201 in insert 141 and out the ring tip 147 through passage 172. When the unilumen tube 134 has nearly all been pulled through the anode ring 135, the free end of coil conductor 74 is inserted into passage 265 of bilumen tube 122 from the distal end 267 thereof (FIG. 10). Coil conductor 74 is then threaded and pulled through passage 265 until tube 122 telescopes into ring body 145 and abuts proximal end 193 of anode insert 141, while at the same time the remainder of unilumen tube 134 is pulled through the anode ring 135. The cathode coil conductor 75 is then inserted into the passage 136 (FIG. 10) in the free end of unilumen tube 134, and is threaded and pulled through the unilumen tube 134 and into and through the connected passage 127 of bilumen tube 122.

As an aid in threading and pulling conductors 74, 75 through their respective passages in the insulation tubes 122, 134, a stiff, solid wire may first be inserted into and threaded through such passages and attached to the coil conductor, as by hooking the wire through a coil turn and twisting it back upon itself. Then, the wire and attached coil conductor may be pulled or "fished" back through the insulation tube passage, whereupon the wire is removed from the coil conductor.

The cathode coil conductor 75 is then connected to the cathode tip 137 in the manner as shown in FIG. 3. The conductor 75 is inserted into a blind socket passage 269 in socket stem 270 of cathode tip 137 until it reaches a junction 271 where the passage 269 begins narrowing conically to its blind end. The conductor 75 is then crimped securely in place by two trapezoidal crimps 273 impressed on opposite sides of the socket stem 270 in like manner as conductor 74 is crimped to the anode insert 141. The free end of the unilumen tube 134 is then stretched or lapped as at 275 over the end of the socket stem 270. The cathode connection is completed by molding or vulcanizing a frustum-shaped potting hood 277 of silicone rubber around most of the length of the cathode tip 137 and around a portion of unilumen tube 134, thereby covering socket stem 270, the lapped-over end 275 of unilumen tube 134 and a portion of tube 134 extending proximally of lapped-over end 275.

Assembly of the anode insert embodiment is completed by molding or vulcanizing potted regions 213, 215 onto the insulation tubes 122, 134 and the anode ring 135; attaching conductors 74, 75 to pin plugs 95, 97; and molding or vulcanizing casing 79 to pin plugs 95, 97 and to bilumen tube 122, all as previously described.

It should be noted that unlike previously existing devices, the catheter conductor 75 is oriented to center by the geometry of the anode ring 135 (FIG. 3). Also, by assembling the electrode portion of the invention in the above manner, the resulting molded assembly will be straight and free of twists or bends caused by unequal coil conductor tensions common in previous devices. Thus, the electrodes of the anode insert embodiment of the invention may be implanted in an internal organ of an animal with relative ease.

3. Anode Ring of the Second Embodiment

Figure 16:
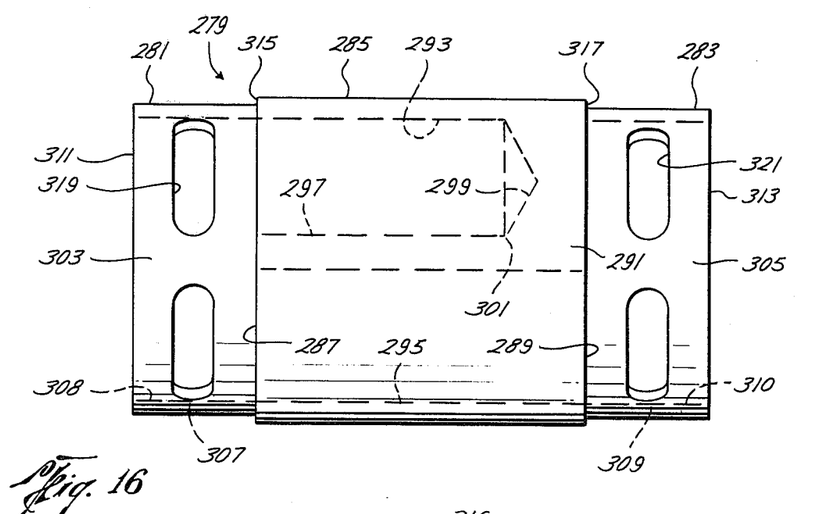
FIG. 16 is an enlarged, planar view of the anode ring of a second embodiment of the invention.
Figure 17:
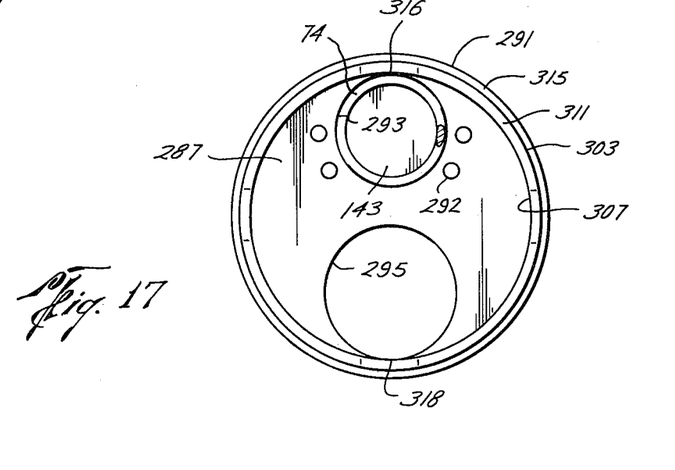
FIG. 17 is an enlarged, end view of the anode ring of the second embodiment of the invention.

The configuration of the anode ring of the second embodiment of the invention is shown in FIGS. 16 and 17. Unlike the anode insert embodiment, the second embodiment uses no separate anode insert; the anode ring is a single, integral piece. However, as in the case of the anode insert embodiment, when the second embodiment of the invention is employed the distal end of insulation tube 78 has the configuration shown in FIG. 10 and described above. Also, the crimp slug shown in FIG. 9 and used in assembling the anode insert embodiment is used in like manner in assembling the second embodiment.

Referring particularly to FIG. 16, the anode ring of the second embodiment of the invention is shown generally at 279. Anode ring 279 is made of a body-compatible implantable metal and includes bilumen and unilumen anchoring extensions 281, 283, respectively, and main ring body 285. Main ring body 285 is generally of right circular cylindrical shape and has proximal end 287, distal end 289 and outer surface 291.

Main ring body 285 furter has blind passage 293 and channel 295. Blind passage 293 extends from proximal end 287 of ring body 285 through most, but not all, of the length of ring body 285 in a direction parallel to the axis of ring body 285. Blind passage 293 includes cylindrical portion 297 and conical portion 299 with junction 301 therebetween. Cylindrical portion 297 has a diameter slightly greater than the diameter of conductor 74. The axis of passage 293 is spaced from the axis of main ring body 285 a distance greater than the radius of cylindrical portion 297. Conical portion 299 is formed when passage 293 is drilled.

Channel 295 is cylindrical in shape and extends through the entire length of ring body 285 in a direction parallel to the axis of ring body 285. The diameter of channel 295 is substantially greater than the diameter of conductor 75 and is slightly greater than the diameter of unilumen tube 134. The axis of channel 295 is spaced from the axis of ring body 285 a distance greater than the radius of channel 295. The axis of channel 295 is aligned with the axes of passage 293 and ring body 285, i.e. the axes are all perpendicular to a common diameter.

Bilumen anchoring extension 281 and unilumen anchoring extension 283 are generally right circular cylindrical tubular members of constant wall thickness that are co-axial with and integral with ring body 285, and that protrude axially outward from the respective proximal and distal ends 287, 289 of ring body 285. Anchoring extensions 281, 283 have respective outer surfaces 303, 305 and respective inner surfaces 307, 309 which define passages 308, 310. Bilumen anchoring extension 281 has proximal end 311. Unilumen anchoring extension 283 has distal end 313.

The outer diameter of extension 281 is equal to the outer diameter of extension 283, both of which are less than the outer diameter of main ring body 285, whereby annular shoulders 315, 327 exist at the ends 287, 289, respectively, of ring body 285. Shoulders 315, 317 extend from the outer surface 291 of ring body 285 to the respective outer surfaces 303, 305 of bilumen and unilumen anchoring extensions 281, 283. The inner diameters of extensions 281, 283 are also equal, and are slightly larger than the outer diameter of bilumen tube 122.

Channel 295 and passage 293 are spaced from the outer surface 291 of ring body 285 a distance such that their cylindrical surfaces are approximately internally tangent to the inner surface 307 of extension 281 at end 287 of ring body 285, as shown at 316, 318 in FIG. 17.

Extensions 281, 283 are each provided with a plurality of anchor slots 319, 321, respectively, spaced about their circumferences. Anchor slots 319, 321 extend completely through the walls of extensions 281, 283 from outer surfaces 303, 305 to inner surfaces 307, 309, respectively. Anchor slots 319, 321 may have their circumferential dimension substantially greater than their axial dimension as shown in FIG. 16, or they may be circular, or they may have other shapes. Anchor slots 319, 321 are similar to the previously described apertures 163, 189 in anode ring 135, and serve the same purpose, i.e. to anchor silicone rubber potting material to the anode ring and to the bilumen and unilumen insulation tubes.

In order to promote adhesion between the silicone rubber potting material to be added as described below and the anode ring 279, the inner surfaces 307, 309 and the outer surfaces 303, 305 of anchoring extensions 281, 283 and ends 287, 289 of ring body 285 are roughened by chemical etching or blasting or other process in like manner as inner surface 155 of ring body 145 and outer surface 169 of ring tip 147. Further, as in the case of ring tip 147, the extended lengths of the anchoring extensions 281, 283 also help promote a strong bond between the potting material and the anode ring.

Assembly of a catheter using the anode ring of the second embodiment of the invention is the same in many respects as assembly using the anode insert embodiment and described above in detail. Where assembly is the same for both embodiments it will be noted, and the prior description will not be repeated here. Where there are differences, they will be described in detail.

Attachment of conductor 74 to anode ring 279 is carried out in a similar manner as attachment of conductor 74 to insert 141. A slug 143 is inserted into the end of the conductor 74, and the conductor end with the inserted slug is then inserted into passage 293 of ring body 285 as far as junction 301. The conductor 74 is then securely crimped in place inside passage 293 with four pit-shaped crimps 292 impressed into the end face 287 of ring body 285. Crimps 292 are placed in the end face 287 rather than in outer surface 291 because no scratches or other interruptions should be present in surface 291. To impress crimps 292 into face 287, the end of a driving pin having raised portions correlative in shape to crimps 292 is placed against face 287 of ring 279 while ring 279 is held in a split cavity vise machined to the dimensions of ring 279, and then sufficient downward axial force is applied to the driving pin to produce crimps 292. Thus, a firm, reliable mechanical and electrical connection is provided between conductor 74 and anode ring 279.

At this point, unilumen tube 134 is threaded and pulled through passage 308, channel 295 and passage 310 of anode ring 279. Before tube 134 is pulled as far as posible through ring 279, i.e. before bilumen tube 122 abuts end 287 of ring body 285, conductor 74 is inserted into passage 265 of tube 122 at the distal end 267 thereof. Conductor 74 is then threaded and pulled through passage 265 in the manner as previously described until bilumen tube 122 telescopes into extension 281 and abuts end 287 of ring body 285. At the same time, tube 134 is pulled the rest of the way through ring 279 to eliminate any slack therein. Conductor 75 is then threaded and pulled through passage 136 of unilumen tube 134 and the connected passage 127 of bilumen tube 122 in the manner as previously described. Note that with coil conductor 75 in place in unilumen tube 134 and the connected bilumen tube 122, the walls of tubes 122, 134 electrically insulate the conductor 75 from the conductor 74 and the anode ring 279.

After coil conductors 74, 75 are threaded and pulled into their respective passages in tubes 122, 134, conductors 74, 75 are attached to pin plugs 95, 97; casing 79 is molded or vulcanized to pin plugs 95, 97 and to bilumen tube 122; conductor 75 is attached to cathoe tip 137; and potting hood 277 is molded or vulcanized onto the cathode tip 137 and the unilumen tube 134, all as previously described, and silicone rubber potting material is molded or vulcanized onto both ends of the anode ring 279 and onto portions of the insulation tubes 122, 134 protruding therefrom similarly to potted regions 213, 215 shown in FIG. 4 and described previously. The rubber potting material is formed completely around the anchoring extensions 281, 283 to a level flush with the outer surface 291 of ring body 285, and abutting the annular shoulders 315, 317. The potting material also extends through and completely fills the anchoring slots 319, 321, and further extends into passages 308, 310, completely filling any spaces between tubes 122, 134 and the inside surfaces 307, 309 of extensions 281, 283, and between tube 122 and proximal end 287 of ring body 285. The potting material also extends away from the anode ring around portions of tubes 122, 134, tapering to a feathered edge on the tubes as shown at 219, 223 in FIG. 4 and described previously. Thus, a secure, firm and reliable body fluid-resistant mechanical and electrical connection is obtained between conductor 74 and anode ring 279, and between conductor 75 and cathode tip 137. Conductor 75 is also securely electrically insulated from conductor 74.

4. Anode Ring of the Third Embodiment

Figure 18:
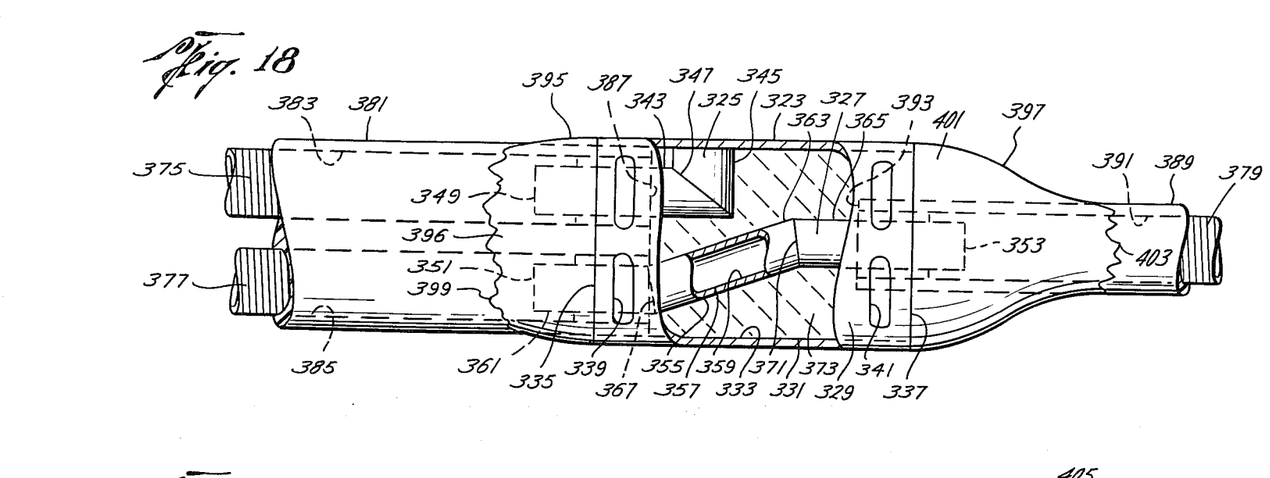
FIG. 18 is an enlarged, partially sectional view of the electrode portion of a third embodiment of the invention.

The configuration of the anode ring of the third embodiment of the invention, or the feed-through anode ring, is shown in FIG. 18. The cathode tip used in the third embodiment is the same as that shown in FIG. 3 and used in both the anode insert embodiment and the second embodiment of the invention, and will not be discussed here.

Referring to FIG. 18, feed-through anode ring includes anode ring body 323, anchor post 325 and feed-through tube 327, all made from a body-compatible, implantable metal.

Anode ring body 323 is a right circular cylindrical tubular member of uniform wall thickness having an outer cylindrical surface 329, an inner cylindrical surface 331 defining a passage 333, an annular proximal end 335 and an annular distal end 337. Near proximal and distal ends 335, 337 anode ring 323 is provided with a plurality of circumferentially spaced apertures 339, 341, respectively. Apertures 339, 341 extend entirely through the wall of tubular anode ring body 323 from outer surface 329 to inner surface 331 and may have their circumferential dimension substantially greater than their axial dimension as shown in FIG. 18, or they may be circular, or they may have other shapes. Apertures 339, 341 are like the previously described apertures 163 in anode ring 135 and serve the same purpose, i.e. to anchor silicone rubber potting material to the anode ring and to the bilumen and unilumen insulation tubes.

The inner surface 331 of anode ring body 323 is roughened in like manner as the previously described surfaces 155, 169 of anode ring 135 in order to promote adhesion between the ring body 323 and the silicone rubber potting material and ceramic insulation to be added as described below.

Anchor post 325 is a solid, integral L-shaped member having a shank 343 and a foot 345 of circular cylindrical configuration which form a right angle bend 347 at their juncture. The foot 345 of post 325 is integral with the ring body 323 and extends from inner surface 331 thereof at a location distally axially spaced from apertures 339, radially inward into passage 333 a distance short of the longitudinal axis of ring body 323. Shank 343 extends longitudinally of and parallel to the ring body 323 from its juncture 347 with foot 345 to its proximal end 349, which protrudes a substantial distance from the end 335 of ring body 323 in a proximal direction.

Feed-through tube 327 is a segmented, open ended tube of uniform wall thickness having a proximal end 351, a distal end 353 and generally circular cylindrical outer and inner surfaces 355, 357, respectively, inner surface 357 defining a passage 359. Tube 327 comprises a proximal segment 361, a jogged segment 363 and a distal segment 365. Proximal segment 361 is parallel to ring body 323 and extends from proximal end 351 into the ring body 323 to its juncture 367 with jogged segment 363, which juncture is slightly distally axially spaced from apertures 339. Proximal end 351 of tube 327 protrudes from end 335 of ring body 323 the same distance as end 349 of anchor post shank 343. Jogged segment 363 extends from juncture 367 at an angle to proximal segment 361 toward the longitudinal axis of ring body 323 to juncture 371 between jogged and distal segments 363, 365. Juncture 371 lies in a plane containing the intersection of the longitudinal axes of segment 363 and ring body 323. Distal segment 365 extends from juncture 371 at an angle to jogged segment 363 and coaxial with the anode ring body 323 to the feed-through tube's distal end 353, which protrudes a substantial distance beyond distal end 337 of ring body 323.

Feed-through tube 327 is supported within the ring body 323 by a core 373 of electrically insulative heat resistant material such as, for example, porcelain or other ceramic, alumina, or epoxy. Insulative core 373 fills the entire passage 333 in ring body 323 between two planes perpendicular to the longitudinal axis of ring body 323 and located slightly distally of apertures 339 and slightly proximally of apertures 341, respectively. Insulative core 373 electrically insulates feed-through tube 327 from ring body 323 and anchor post 325.

The anode ring of the third embodiment of the invention further includes anode coil conductor 375, cathode lead coil conductor 377 and cathode tip coil conductor 379. Coil conductors 375, 377 and 379 comprise tightly wound spirals of wire like previously described conductors 74, 75. Conductor 375 has an inner diameter slightly greater than the diameter of shank 343 of post 325. Conductors 377 and 379 have inner diameters slightly greater than the outer diameters of segments 361, 365, respectively, of tube 327.

Conductor 375 is attached at one end to one of pin plugs 95, 97; the other end of conductor 375 is lapped over end 349 of shank 343 and extends part way along the length of shank 343, but not as far as end 335 of ring body 323. Conductor 377 is attached at one end to the other of pin plugs 95, 97; the other end of conductor 377 is lapped over end 351 of feed-through tube segment 361 and extends part way along the length of segment 361, but not as far as end 335 of ring body 323. One end of conductor 379 is attached to the cathode tip 137 as shown in FIG. 3 and as previously described; the other end of conductor 379 is lapped over end 353 of feed-through tube segment 365 and extends part way along the length of tube segment 365, but not as far as end 337 of ring body 323.

Shank 343 and tube segment 361 are disposed with their respective longitudinal axes spaced from the longitudinal axis of ring body 323 a distance greater than the outside radii of their attached conductors 375, 377. Tube segment 365 is coaxial with ring body 323 and, therefore, conductor 379 is also coaxial with ring body 323.

Conductors 375, 377 and 379 are electron-beam welded to shank 343, tube segment 361 and tube segment 365, respectively. Elecrtron-beam welding of this type is carried out in a high vacuum environment and results in a strong, secure and reliable connection. Thus, conductor 375 is securely connected to anode ring 323 through integral post 325, and conductor 377 is securely connected to conductor 379 through tube 327. When electron-beam welding is used to attach the conductors to the anode ring, insulative core 373 should not be made of silicone rubber, which breaks down under the high temperatures, which may be greater than 1000° F., accompanying the welding process. However, the insulative materials discussed above such as ceramic, alumina or epoxy will withstand such high temperatures with no adverse effects.

Conductors 375, 377 are sheathed in a bilumen, silicone rubber insulation tube 381 which is like bilumen tube 122, except that tube 381 has no unilumen tube molded or vulcanized to one end as does tube 122. Tube 381 has a diameter less than the diameter of passage 333 of ring body 323, and has passage 383 carrying conductor 375, and passage 385 carrying conductor 377. End 387 of tube 381 is telescoped into passage 333 of anode ring 323 from end 335 thereof, with shank 343 and tube segment 361 in turn being telescoped into passages 383, 385, respectively, of tube 381. End 387 of tube 381 extends into ring body 323 past the apertures 339 but just short of the insulative core 373.

Conductor 379 is sheathed in a unilumen, silicone rubber insulation tube 389 which is like unilumen tube 134, except that tube 389 is not molded or vulcanized at one end to a bilumen tube, as is tube 134. Tube 389 has passage 391 carrying conductor 379. End 393 of tube 389 is telescoped into passage 333 of anode ring body 389 from end 337 thereof, with tube segment 365 in turn being telescoped into passage 391 of tube 389. End 393 of tube 389 extends into ring body 323 past the apertures 341 but just short of the insulative core 373.

The anode ring of the third embodiment of the invention further includes silicone rubber potted regions 395, 397. Potted region 395 includes a first portion 396 disposed completely circumferentially around bilumen tube 381, and having one end abutting end 335 of ring body 323 and extending therefrom along the length of tube 381 until terminating at a feathered edge 399. The outer diameters of the first portion 396 of potted region 395 and ring body 323 are substantially the same at their interface; the outer diameter of such first portion then decreases or tapers gradually moving away from such interface until it is substantially the same as the outer diameter of tube 381 at feathered edge 399.

Potted region 395 also includes a second portion integral with such first portion 396 and extending therefrom into passage 333 of ring body 323 and entirely filling any spaces around tube 381 between its outer walls and the inner surface 331 of ring body 323; around shaft 343 of anchor post 325, including the area inside passage 383 of tube 381; around tube 327, including the area inside passage 385 of tube 381; around tube 327, including the area inside passage 385 of tube 381; between the end 387 of tube 381 and the adjacent end of insulative core 373; and into and completely filling apertures 339 to a level flush with the outer surface 329 of ring body 323, thus forming a smooth, continuous cylindrical outer surface for ring body 323.

Potted region 397 includes a first portion 401 which abuts distal end 337 of ring body 323 at one of its ends, and from there extends so as to develop a portion of unilumen tube 389 until terminating at a feathered edge 403. The outer diameters of first portion 401 of potted region 397 and ring body 323 are substantially the same at end 337 of ring body 323; the outer diameter then decreases or tapers moving away from end 337 until it is substantially the same as the outer diameter of tube 389 at feathered edge 403. The shape of the outer surface of the first portion 401 of potted region 397 is substantially the same as the shape of the outer surface of potted region 215 shown in FIG. 4 and described above.

Potted region 397 further includes a second portion integral with first portion 401 and extending therefrom into passage 333 of ring body 323 and entirely filling any spaces around tube 389 between its outer walls and the inner surface 331 of ring body 323; around tube 327, including the area inside passage 391 of tube 389; between the end 393 of tube 389 and the adjacent end of insulative core 373; and into and completely filling apertures 341 to a level flush with the outer surface 329 of ring body 323.

In the preferred structure of the third embodiment of the invention with tubes 381, 389 and potted regions 395, 397 all made of silicone rubber, potted regions 395, 397 are vulcanized or molded onto and around the respective tubes 381, 389 so as to be integral therewith, both inside and outside anode ring body 323. Also, potted regions 395, 397 are vulcanized or molded within apertures 339, 341 and onto or around the respective portions of the ring body 323, shaft 343, tube 327 and core 373. Thus, a firm, anchored, separation-resistant adhesive connection is provided between tube 381 and anode ring body 323, and between tube 389 and anode ring body 323.

It should be noted that use of a feed-through tube 327 with its double bend to orient cathode tip conductor 379 to the center or longitudinal axis of ring body 323 eliminates the kinks or open turns that would occur in a continuous cathode conductor if it were bent in such fashion in passing through the ring body.

Tube 327 must be hollow and open ended in order to allow the insertion of a stiff guide wire through the passages in the cathode conductors to the cathode tip 137 to aid in implanting the electrodes in the desired organ of the animal's body.

In assembling the anode ring of the third embodiment of the invention, tube 327 is positioned in its proper orientation with respect to ring body 323 and ring body 323 is then filled to the designated limits with insulative core 373, which hardens to maintain the proper positioning of tube 327 and ring body 323. Conductors 375, 377 and 379 are then telescoped over the protruding ends of shaft 343, tube segment 361 and tube segment 365, respectively, and are electron-beam welded thereto in a high vacuum environment. Conductors 375, 377 and 379 are then threaded and pulled through their respective passages in bilumen and unilumen tubes 381, 389 and tubes 381, 389 are telescoped into the anode ring body 323. Potted regions 395, 397 are then molded or vulcanized onto the anode ring assembly.

A catheter according to the third embodiment of the invention is completed by attaching conductor 379 to cathode tip 137 and molding or vulcanizing potting hood 277 thereon; attaching conductors 375, 377 to pin plugs 95, 97; and molding or vulcanizing casing 79 onto pin plugs 95, 97 and bilumen tube 381, all as previously described.

5. Anode Ring of the Fourth Embodiment

Figure 19:
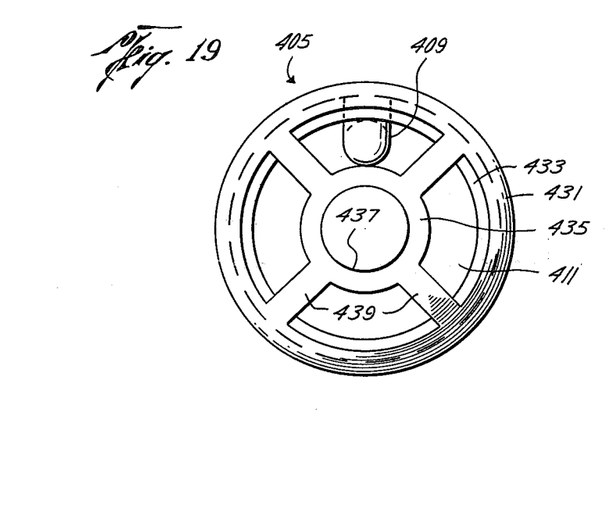
FIG. 19 is an enlarged end view of the anode ring of a fourth embodiment of the invention.
Figure 20:
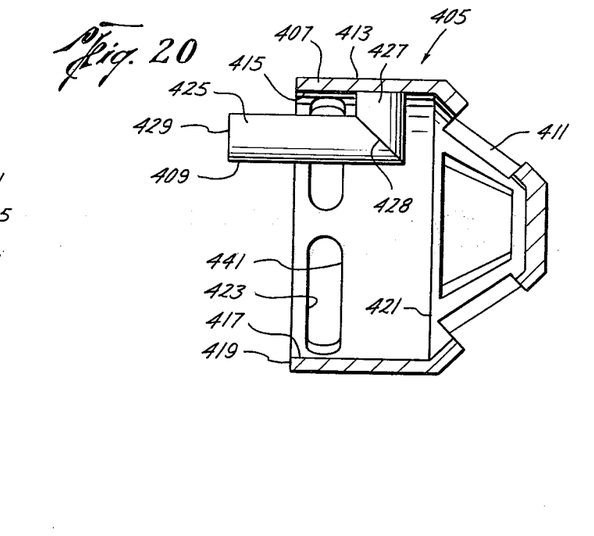
FIG. 20 is an enlarged, sectional view of the anode ring of the fourth embodiment of the invention.

The configuration of the anode ring of the fourth embodiment of the invention is shown in FIGS. 19 and 20. The anode ring of the fourth embodiment includes features similar to features previously described in connection with the other three embodiments, such as the conical ring tip of the first embodiment and the anchor post of the third embodiment.

Also, when a catheter constructed according to the invention utilizes the anode ring of the fourth embodiment, the conductors have the configurations of coil conductors 74, 75; the insulation tubes have the configurations of tubes 122, 134; and the cathode tip has the configuration shown in FIG. 3, all as previously described.

Referring to FIGS. 19 and 20, anode ring 405 is a single, integral member of body-compatible, implantable metal and comprises a ring body 407, an anode conductor anchor pin 409 and a ring tip 411. Ring body 407 is generally of right circular cylindrical tubular configuration having a uniform wall thickness and having a cylindrical outer surface 413, a cylindrical inner surface 415 which defines a passage 417, an annular proximal end 419 and an annular distal end 421. Ring body 407 also includes a plurality of circumferentially spaced apertures 423 near and set in from proximal end 419. Apertures 423 extend completely through the wall of anode ring body 407 from outer surface 413 to inner surface 415. Apertures 423 are preferably the same shape as the previously described apertures 163 and serve the same function, i.e. to anchor silastic potting material to the anode ring and to the insulation tubes carrying coil conductors either to or through the anode ring.

Anchor pin 409 is preferably the same shape as post 325 shown in FIG. 18 and previously described, and includes a shaft 425 and a stem 427. Stem 427 and shaft 425 form a right angle bend at their juncture 428 and are integrally interconnected at such juncture. Stem 427 is integrally connected to anode ring body 407 and extends radially inward from the inner surface 415 of ring body 407 between apertures 423 and distal end 421 a distance less than the radius of passage 417. Shaft 425 extends from juncture 428 longitudinally axially of and parallel to ring body 407 to end 429, which protrudes a substantial distance beyond the end 419 of ring body 407 in a proximal direction. Shaft 425 of anchor pin 409 has an outer diameter slightly less than the diameter of the passage in coil conductor 74.

Anode ring tip 411 includes a rim 431 having the shape of a hollowed-out frustum or a conical annulus and is integrally connected at its base to distal end 421 of ring body 407. The walls of rim 431 are of the same thickness as the walls of ring body 407. The outer diameter of rim 431 at end 421 is the same as the outer diameter of ring body 407, and decreases linearly moving distally of ring body 407 until reaching distal face 433. Distal face 433 of rim 431 is dished, i.e. is concavely beveled (FIG. 20).

Anode ring tip 411 further includes an annular cylindrical eye 435 having an outside diameter substantially smaller than the inside diameter of rim 431 at face 433. Annular eye 435 defines an opening 437 that is slightly larger than the diameter of insulation tube 134. Eye 435 is distally axially spaced from ring body 407 and rim 431, and is coaxial therewith.

Ring tip 411 also includes a plurality of elongate spokes 439 of solid rectangular cross section connected at one end to rim 431 and at the other end to eye 435. Spokes 439 are preferably uniformly angularly spaced about the circumferences of the rim 431 and the eye 435, and support the eye in its proper position axially spaced from the rim 431 and the anode ring body 407.

In assembling a catheter utilizing the anode ring of the fourth embodiment of the invention, coil conductor 74 is first attached to anchor pin 409 by slipping the coil end over end 429 of pint 409 and sliding it part way along the length of shaft 425, stopping short of end 419 of ring body 407. The coil 74 is then electron beam-welded onto shaft 425 of pin 409, thereby securely connecting conductor 74 to ring body 407. Unilumen tube 134 is then threaded through passage 417 of ring body 407 from the proximal end 419 through the distal end 421, and then through opening 437 in eye 435. Conductor 74 is threaded through passage 265 of bilumen tube 122 from the distal end 267 thereof until the end of bilumen tube 122 telescopes into passage 417 of ring body 407, shaft 425 of pin 409 telescoping into passage 265 of tube 122. The end of tube 122 telescopes into passage 417 at least as far as distal edges 441 of apertures 423. Conductor 75 is then fished through passages 136, 127 are previously described. Silicone rubber potting material is then molded or vulcanized at both ends of anode ring 405, enveloping adjacent portions of tubes 122, 134 and extending part way along their lengths to feathered edges; extending into and entirely filling any spaces remaining in passage 417 of ring body 407, including in areas between tubes 122, 134 and inner surface 415 of ring body 407, and inside passage 265 of tube 122 arround shaft 425; extending into and entirely filling apertures 423 to a level flush with outer surface 413 of ring body 407; and completely enveloping ring tip 411, both on the inside and the outside including surrounding spokes 439 and filling the spaces therebetween, and surrounding eye 435 and filling any space between tube 134 and the surface of opening 437.

Assembly is completed by connecting conductor 75 to cathode tip 137 and adding potting hood 277; connecting conductors 74, 75 to pin plugs 95, 97; and adding casing 79 to pin plugs 95, 97 and tube 122, all as previously described.

6. Use of the Invention

In using a catheter constructed according to the invention, the required medical and surgical procedures, which may include implanting electronic unit 49, are carried out preparatory to implanting the bipolar electrode tip in the desired region of the animal's body. A stiff guide wire is then inserted through the passages in pin plug 97 and, as the case may be, in coil conductor 75 or in coil conductors 377, 379 and feed-through tube 327 to cathode tip 137. The bipolar electrode tip is then inserted into the animal's body and, with the aid of the guide wire, is threaded through a blood vessel or other means until the desired implant region is reached. The electrode tip is then implanted into the tissue at the desired region, again with the aid of the guide wire. The guide wire is then removed, and the pin plugs 95, 97 are connected to electronic unit 49, whereupon the system may begin transmitting electrical signals to and from the desired region.

Because many varying and different embodiments may be made within the scope of the inventive concept herein taught, and because many modifications may be made in the embodiments herein detailed, it should be understood that the details described herein are to be interpreted as illustrative and not in a limiting sense.

What is claimed is:

1. An electrode assembly for a catheter having a cathode tip, a first conductor and a second conductor, comprising:

an anode ring having a longitudinal axis, a proximal end and a distal end, and including an outer portion and an inner portion connected to said outer portion, said outer portion including a ring body and said inner portion including an anode insert telescopically received in and frictionally retained in said ring body, one terminal end of such first conductor being disposed entirely within said anode insert, said anode insert including coupling means for mechanically coupling said anode insert of said inner portion to such one terminal end of such first conductor and passing means for passing such second conductor through said anode ring from said proximal end of said anode ring to said distal end of said anode ring, one terminal end of such second conductor being connected to such cathode tip, such cathode tip being spaced distally of said anode ring, said anode insert of said inner portion including a solid member having a proximal end and a distal end, said coupling means including a blind passage extending from said proximal end of said member through a part of the length of said member, such one terminal end of such first conductor being disposed in said blind passage, there being a pair of elongate trapezoidal crimps impressed into said member on opposite sides of said blind passage against such one terminal end of such first conductor, said passing means including a channel extending through said solid member from said proximal end of said member to said distal end of said member, such second conductor being carried within said channel.

2. An electrode assembly according to claim 1, such one end of such first conductor having a passage therein, and including a solid slug disposed in such passage in such one end of such first conductor for providing solidarity and rigidity for such one end of such first conductor at the location of said crimps.

3. An electrode assembly according to claim 1, and including potting means disposed on said anode ring for potting said anode ring, said outer portion of said anode ring including anchoring means for anchoring said potting means to said anode ring.

4. An electrode assembly according to claim 3, said ring body of said outer portion of said anode ring being tubular and having a wall with an outer surface and an inner surface, said anchoring means including an aperture extending through said wall of said tubular ring body from said outer surface to said inner surface of said wall.

5. An electrode assembly according to claim 4, said anchoring means including a plurality of circumferentially spaced apart apertures extending through said wall of said tubular ring body from said outer surface to said inner surface of said wall.

6. An electrode assembly according to claim 3, said outer portion of said anode ring including inner and outer surfaces, said anchoring means including some portions of said inner and outer surfaces being roughened.

7. An electrode assembly for a catheter having a cathode tip, a first conductor and a second conductor, comprising:

an anode ring having a longitudinal axis, a proximal end and a distal end, and including an outer portion and an inner portion connected to said outer portion, said outer portion including a ring body and said inner portion including an anode insert telescopically received in and frictionally retained in said ring body, one terminal end of such first conductor being disposed entirely within said anode insert, said anode insert including coupling means for mechanically coupling said anode insert of said inner portion to such one terminal end of such first conductor and passing means for passing such second conductor through said anode ring from said proximal end of said anode ring to said distal end of said anode ring, one terminal end of such second conductor being connected to such cathode tip, such cathode tip being spaced distally of said anode ring, said anode insert of said inner portion including a solid member having a proximal end and a distal end, said coupling means including a blind passage extending from said proximal end of said member through a part of the length of said member, such one terminal end of such first conductor being disposed in said blind passage, there being a pair of elongate trapezoidal crimps impressed into said member on opposite sides of said blind passage against such one terminal end of such first conductor, said passing means including a channel extending through said solid member from said proximal end of said member to said distal end of said member, such second conductor being carried within said channel, said channel carrying such second conductor therewithin such that the longitudinal axis of such second conductor is spaced from said longitudinal axis of said anode ring at said proximal end of said anode ring, said outer portion of said anode ring at said distal end of said anode ring including centering means for orienting such longitudinal axis of such second conductor from its position spaced from said longitudinal axis of said anode ring at said proximal end of said anode ring to said longitudinal axis of said anode ring.

8. An electrode assembly according to claim 7, said centering means including a ring tip having a passage there through, said passage through said ring tip being coaxial with said anode ring, such second conductor being carried within said passage through said ring tip.

* * * * *